US006946252B2

(12) United States Patent
Kambara

(10) Patent No.: US 6,946,252 B2
(45) **Date of Patent: *Sep. 20, 2005**

(54) SAMPLE PREPARATION METHOD AND A SAMPLE PREPARATION APPARATUS FOR DNA ANALYSIS

(75) Inventor: Hideki Kambara, Hachioji (JP)

(73) Assignee: Hitachi, Ltd., Tokyo (JP)

(*) Notice: Subject to any disclaimer, the term of this patent is extended or adjusted under 35 U.S.C. 154(b) by 491 days.

This patent is subject to a terminal disclaimer.

(21) Appl. No.: 10/105,301

(22) Filed: Mar. 26, 2002

(65) Prior Publication Data

US 2002/0102600 A1 Aug. 1, 2002

Related U.S. Application Data

(63) Continuation of application No. 09/587,613, filed on Jun. 5, 2000, now abandoned.

(30) Foreign Application Priority Data

Jun. 9, 1999 (JP) .......................................... 11-162038

(51) Int. Cl.[7] .......................... C12Q 1/68; C12P 19/34; C07H 21/04

(52) U.S. Cl. ............................. 435/6; 435/5; 435/91.2; 435/91.1; 435/24.3; 435/24.33; 935/77; 935/76

(58) Field of Search ............................... 435/5, 6, 91.1, 435/91.2; 536/24.3, 24.33; 935/77, 76

(56) References Cited

U.S. PATENT DOCUMENTS

| | | | | |
|---|---|---|---|---|
| 5,843,660 A | | 12/1998 | Schumm et al. | 435/6 |
| 5,910,406 A | | 6/1999 | Minter | 435/6 |
| 5,925,525 A | | 7/1999 | Fodor et al. | 435/6 |
| 6,054,035 A | | 4/2000 | Kambara | 435/287.2 |
| 6,060,240 A | | 5/2000 | Kamb | 435/6 |
| 6,268,148 B1 | * | 7/2001 | Barany et al. | 435/6 |
| 6,518,027 B2 | * | 2/2003 | Kambara | 435/6 |

FOREIGN PATENT DOCUMENTS

| | | |
|---|---|---|
| EP | 0 846 776 A2 | 12/1997 |
| WO | WO 93/18177 | 3/1993 |
| WO | WO 98/29736 | 12/1997 |
| WO | WO 99/09217 | 8/1998 |
| WO | WO 99/24822 | 11/1998 |

OTHER PUBLICATIONS

European Search Report, EP 00 11 2246. Search completion date Mar. 18, 2002.

U.S. Appl. No. 09/260,543, filed Mar. 2, 1999, DNA Probe Array.

Nucleic Acids Research, 1977, vol. 25, No. 22, pp. 4694–4696.

* cited by examiner

*Primary Examiner*—Kenneth R. Horlick
*Assistant Examiner*—Joyce Tung
(74) *Attorney, Agent, or Firm*—Reed Smith LLP; Stanley P. Fisher, Esq.; Juan Carlos A. Marquez, Esq.

(57) ABSTRACT

A sample preparation apparatus for DNA analysis comprises a holder for separating specific primers on the basis of size, color, weight, dimension, or degree of magnetization, the specific primers having base sequences complementary to a plurality of DNA fragments to be amplified via PCR, and the specific primers being capable of binding respectively to the DNA fragments; and a reaction-solution-holding plate having a concavity which accommodates one edge of the holder and a PCR solution containing a common primer capable of hybridizing with the base sequence of an oligonucleotide introduced into the 5'-end of each of the DNA fragments, and the DNA fragments. The PCR amplification of the DNA fragments is carried out by using the specific primers (immobilized on the surfaces of a plurality of mutually separable supports with respect to each DNA fragments) and the common primer (a mobile primer common to all DNA fragments) to produce PCR amplification products inside the corresponding portions of the holder. The DNA fragments are derived from a plurality of DNAs to be amplified by PCR under the same conditions at the same time to avoid undesired mutual interference among the primers, and the PCR products can be separated and recovered for each of the DNA fragments. The sample preparation method for DNA analysis comprises the relevant amplifying, separating and recovering steps as described above.

1 Claim, 12 Drawing Sheets

SAMPLE PREPARATION METHOD AND A SAMPLE PREPARATION APPARATUS FOR DNA ANALYSIS

This application is a continuation application based on the application Ser. No. 09/587,613 filed on Jun. 5, 2000 now abandoned.

BACKGROUND OF THE INVENTION

A. Field of the Invention

The present invention relates to a method for DNA comparative analysis in a plurality of samples and a sample preparation method for the DNA analysis.

B. Description of the Prior Art

With the progress of genome analysis, the first stage of the genome project, where the analysis of genome structures by DNA sequencing is the major subject, is going to the end and the genome analysis comes to the second stage of understanding gene functions. The genetic information in genome sequences has to be translated to a protein through mRNA. The genes expressed in a cell at some moment can be determined by detecting mRNAs in the cell. Genetic characteristics of individuals are dependent on various differences in their genome sequences. The analysis of mRNAs in cells or tissues and the comparative analysis of DNA sequences for individual genes are necessary for understanding the gene functions. Especially the analysis of species and amounts of mRNAs in cells is important to know what is going on in the cells. Usually, cDNA (complementary DNA), which is produced by complementary strand extension reactions with a DNA polymerase and a primer hybridizing to each mRNA, is used for the analysis instead of mRNA because mRNAs are easily decomposed by RNase that is in cells.

The scanning of all the cDNAs (or mRNAs) in cells or tissues is called as gene expression profiling. As the size of each cDNA is usually very long to be sequenced or to be analyzed by gel electrophoresis, a part of the sequence is selected as the signature sequence of the cDNA to be analyzed. Each of the signature sequences of cDNAs is amplified and analyzed by gel electrophoresis or by hybridization with a DNA probe array. At first, the signature regions of cDNAs are amplified by PCR (Polymerase Chain Reaction) and then the relative abundance of each signature fragment is analyzed. The key point of the method is how to amplify each of signature regions without losing the relative abundance information. The relative abundance information is frequently lost during the PCR process because the amplification factors of each PCR reaction are dependent on the precise conditions and the sequence of the target cDNA fragment. The PCR amplification for plural of target DNA fragments should be carried out simultaneously to keep the amplification conditions the same. However, it is not so easy because the primers used for amplifying the target DNA fragments frequently interact with each other to produce undesired new DNA fragments which disturb the accuracy and reliability of the gene expression profiling.

The present invention relates to a method for carrying out the simultaneous PCR amplification of various cDNA fragments for quantitative cDNA analysis such as gene expression profiling. The invention also relates to the method for recovering PCR products and the sample preparation for DNA diagnostics. In PCR amplification, two primers are designed to hybridize on the template DNA at predetermined positions. The base sequence of the template DNA sandwiched with the two primers is amplified by repetitive complementary strand extension reactions with the primers. The number of copies of the target DNA fragments increases by several orders of magnitude by PCR. In the case of gene expression profiling, a DNA sample contains various cDNAs fragment species. Many should be analyzed quantitatively. The method requires the PCR amplification of plural of target cDNA fragment species simultaneously. When the PCR amplification of a plurality of DNA fragments or sequences is carried out, artificial fragments are frequently produced through unexpected reactions among primers and DNAs. However, the isolation of the amplified components is labor intensive. Consequently, only one pair of primers is used at a time for PCR amplification. When many target DNA fragment species have to be analyzed, many PCR reactions are required. This is very labor intensive.

On the other hand, the comparative analysis for two or more kinds of DNA fragments is an important subject and is extensively investigated. However, since the amplification rate in PCR depends greatly on the reaction conditions, the comparison of groups of DNA fragments which are obtained under different PCR conditions, namely, groups of DNA fragments which are independently obtained by amplification, has been disadvantageous in that it prohibits quantitative investigation. Factors capable of affecting PCR include the reaction temperature, the base sequences of primers, the amounts of reagents, the kinds and amounts of contaminants, etc. It is considerably difficult to make these factors the same for different reactions.

A PCR technique for quantitative and comparative analysis for one DNA fragment species in various samples such as tissues has recently been developed. This method is called adaptor-tagged competitive PCR (ATAC PCR). Now the target of the analysis is the same DNA fragment species in different DNA samples (for example, different sample numbers are used to identify those samples; sample number 1–sample number 9). There are plural of samples containing various DNA species to be compared. The method can carry out comparative analysis of DNA fragment species belonging to different samples by putting tags depending on the samples. The tagging is taken place by changing the lengths of oligomers connected to the DNA fragments as follows. An oligonucleotide having a known base sequence is connected to each end of the DNA fragment species. The known base sequence is composed of a common base sequence for the hybridization of a primer and a tagging base sequence for discriminating the plurality of the samples containing various DNA species. To separate DNA fragment species produced from different samples, the tagging sequences are designed so as that their lengths are different from sample to sample. In ATAC PCR analysis, only one target DNA fragment species in various samples is analyzed at a time. Each sample contains the target DNA fragment sequences at different ratios. The priming site for PCR amplification is also the same for different DNA fragments. The only difference in the targets is the lengths of the tagging sequence region. Consequently, all the target DNA fragments can be amplified at the same amplification rate while the tagging sequences are kept tagged through the amplification. At least one of the primers used in PCR amplification is labeled with fluorophore. The fluorophore labeled DNA fragment amplified by PCR are analyzed by gel electrophoresis coupled with fluorescence detection. The DNA fragments originated from different DNA samples appear in the different positions in an electropherogram which is used for the comparative analysis of the gene expression.

SUMMARY OF THE INVENTION

ATAC PCR is effective when one target DNA fragment species in different DNA samples is comparatively analyzed.

However, when plural of target DNA fragment species in various samples are the targets of comparative analysis, the accurate comparative analysis becomes difficult because unexpected and undesired side reactions frequently occur in a PCR with plural pairs of primers. Various primers in the reaction mixture may interact with DNA fragments other than proper target DNA fragments and may produce unwanted products. This can be overcome by using two types of primers; the first primer is common to all the target DNA fragments and free in a liquid phase, the second primers are specific to the target DNA fragments and is fixed on solid supports. This prevents the interaction between two different specific primers through a PCR reaction. PCR amplification is carried out under the following conditions: the primers specific to the target DNA fragments, respectively, are immobilized on the surfaces of beads or the like so as to be separated on the basis of the kinds of the primers, and the primers having a common base sequence are mobile in a solution. Thus, the production and amplification of undesired DNA fragments other than the target DNA fragments are prevented.

Thus, the target DNA fragment species are mixed and then subjected to PCR simultaneously. The base sequence of the priming site is the same for different DNA fragments, and most of the base sequences subjected to PCR amplification are the same, and the reactions are carried out in one reaction vessel. Therefore, the target DNA fragment species are amplified under the same conditions. Accordingly, the amplification efficiency of the target DNA fragment species is constant so that a quantitative analysis of DNA fragments is possible.

A specific example of analysis requiring quantitative PCR is the above-mentioned cDNA analysis for monitoring gene expression. Sample cDNAs contain various DNA fragments, and information on gene expression as well as gene function is obtained via quantitative analysis of these DNA fragments in various samples. Usually the copy numbers of target DNAs in samples are small, so that measurement is carried out after PCR amplification.

The PCR amplification should be carried out so as to permit quantitative investigation, and the DNA fragments are preferably reacted at the same time in the same reaction vessel. The PCR conditions should not be different for the DNAs. The PCR amplification of a plurality of DNA species at the same time has been attempted. But it is often unsuccessful because of, for example, the production of unexpected PCR products. On the other hand, when the PCR amplification is carried out for each DNA species independently, the analysis is very labor intensive and troublesome. Further, in gene expression profile analysis, when a uniquely expressed DNA fragment is found, it is preferably taken out for precise analysis.

The recovery of such a DNA fragment from the mixed products has not been carried out because of its difficulty.

Such a situation is common to analyses for diagnoses using genes. Quantitative PCR is important in gene diagnosis and gene expression analysis. The quantitative PCR can easily be carried out, for example, when there is only one target DNA species to be processed in order to find out the presence ratio of the target gene in various environments or in various tissues.

As described above, methods such as ATAC PCR invented for solving this problem are disadvantageous in that they do not permit simultaneous analysis for plurality of target DNA fragment species. It has been an important subject to develop a method for quantitative and comparative analysis of a plurality of target DNA fragment species in various DNA samples, or a sample preparation method.

The present invention is intended to provide a sample preparation method and a sample preparation apparatus which solve the above problems.. In detail, the present invention is intended to provide a sample preparation method and a sample preparation apparatus, in which mutual interference by primers is avoided, and artificial DNA fragment production by primer extension is reduced, therefore a plurality of target DNA fragments from various DNA samples are amplified by PCR simultaneously in one reaction vessel.

In the sample preparation method of the present invention, although a plurality of target DNA fragment species are amplified in one reaction vessel, mutual interaction of primers is prevented by carrying out the PCR amplification in mutually isolated places for the target DNA fragment species, respectively. Primers (specific primers) hybridizing specifically to the target DNA fragment species, respectively are immobilized on surfaces of fine particles or beads, and target DNA fragment species are amplified by PCR on the surfaces of the corresponding fine particles or beads. Each of the specific primers immobilized on fine particles or beads, and a primer (this primer is referred to as a mobile (or free) primer or a common primer) in the liquid phase are used for complementary strand extension.

In addition, mutual interaction of the primers is prevented by localizing the positions of holding the fine particles or beads in the vessel, depending on the kinds of the specific probes (primers) immobilized on the surfaces of the fine particles or beads. the like are separated and recovered, and DNA fragment species trapped on the surfaces of the solid supports are also separated and recovered. The specific primers have substantially the same length but have different base sequences according to their target DNA fragment sequences.

In analysis using the sample preparation method of the present invention, the discrimination of DNA target fragments in various DNA samples is made possible by bonding different kinds of oligomers as priming regions to the ends of target DNA fragments, respectively, according to the DNA samples.

As to the recovery of the PCR products separately according to their kinds, fine particles or beads, which can be discriminated from each other by a chemical or physical property, are used. Each distinguishable fine particle or bead immobilizes the specific primers, specific to a target DNA fragment, on the surface to hold the corresponding DNA fragments amplified through PCR. The fine particles or beads having different chemical or physical properties hold the different kinds of DNA fragments (PCR products) on their surface and are separated by the chemical or physical properties. Consequently the different DNA fragment species or DNA fragment groups produced by PCR are recovered separately with the fine particles or beads. The recovered DNA fragments are analyzed by gel electrophoresis or DNA probe array and so on. Of course the DNA fragments recovered from each kind of fine particles or beads contains DNA fragment copies originated from different DNA samples. The presence ratio of the target DNA fragments among the DNA samples is the same as that of the original one as explained above. The DNA fragments originated from different DNA samples can be distinguished by their lengths because the lengths of the oligomers connected to the target DNA fragment termini differ from DNA sample to DNA sample. This permits the quantitative analysis of the target DNA fragment abundance in various DNA samples.

The sample preparation method of the present invention can be utilized also for carrying out simultaneous PCR amplification of various kinds of target DNA fragments in a plurality of DNA samples to be inspected each containing a plurality of target DNA fragments, and for separating the PCR products. That is, specific primers are immobilized on fine particles or beads and the reactions are carried out in one vessel, or the fine particles or beads are located in different compartments on the basis of the kinds of probes and the PCR amplification is carried out for each of target DNA fragments so that mutual interference of primers may be reduced. After the amplification, the PCR products can be separated and recovered on the basis of the kinds of the DNA fragments and can be analyzed. Of course a DNA probe array can be used as the specific primer support instead of beads.

The sample preparation method of the present invention can provide a method which is impossible according to the referenced prior art, i.e., a method for amplifying the number of copies of a plurality of DNA fragment species derived from a plurality of DNAs amplified while keeping the amplified DNA fragment species quantitatively and comparatively analyzable. According to prior arts, the separation and recovery of PCR amplification products of target DNA fragment species require much labor and time and moreover, the separation and recovery are difficult because gel separation cannot be employed when the DNA fragments have the same length. On the other hand, the separation and recovery can easily be carried out in the present invention.

In the sample preparation method of the present invention, when the base sequences of a plurality of amplified DNA fragment species are determined, sample preparation for the plurality of the amplified DNA fragment species is carried out in one lot in one vessel, and the products are separated and collected for each noted DNA fragment species. Then base sequence determination reaction is carried out for each DNA fragment species, and the reaction products are subjected to gel electrophoresis, whereby the base sequences of the plurality of the DNA fragment species can be determined very efficiently.

The characteristics of typical constitutions of the present invention are explained below. The sample preparation method of the present invention comprises a step of amplifying two or more kinds of target DNA fragments by PCR by using each of specific primers which have base sequences complementary to the target DNA fragments to be amplified and are immobilized on the surfaces of one or more mutually separable groups of supports so as to be separated on the basis of the kinds of the complementary base sequences, and a mobile (free) primer presenting in a solution; and a step of separating and recovering the PCR amplification products, as groups each containing one or more kinds of target DNA fragments.

The sample preparation method of the present invention is characterized also by the following. The mobile (free) primer is a common primer that hybridizes with the two or more kinds of the target DNA fragments in common. The common primer hybridizes with the base sequence of an oligonucleotide introduced into the termini of each of the target DNA fragments. The supports immobilizing the specific primers are a plurality of fine particles or beads, which can be distinguished by specific gravity (weight), color, or size. The kinds of the specific primers immobilized on a bead can be known by the specific weights, respectively, or sizes, of the supports, or colors.

Alternatively, the supports are a plurality of fibers, and the specific primers are immobilized near the ends of different fibers so as to be separated on the basis of the kinds of the specific primers. In particular, the supports are a plurality of mutually discriminable fine particles or beads, which are held in a single reaction cell. The supports are separately held in different compartments in a single capillary.

The fine particles immobilizing the primers are separately held in groups through dummy beads or dummy fine particles, which separate a plurality of compartments. The supports are a plurality of fine particles or beads, which can be discriminated as a plurality of groups which can be discriminated on the basis of the difference of any of the sizes of the fine particles or beads, the specific weights of the fine particles or beads, colors given to the fine particles or beads, and the degrees of magnetization of the fine particles or beads.

The sample preparation method of the present invention comprises a step of amplifying a plurality of target DNA fragments by PCR by using each of the specific primers which have, respectively, base sequences complementary to the two or more kinds, respectively, of the DNA fragments to be amplified, are immobilized on the surface of one or more mutually separable groups of supports so as to be separated on the basis of the kinds of the- complementary base sequences, and a free primer in a solution; and a step of separating and recovering the PCR amplification products on the basis of the kinds of DNA fragments.

The free primer is a common primer that hybridizes with the two or more kinds of the DNA fragments in common at an oligonucleotide portion introduced into the end of each DNA fragment.

The sample preparation apparatus as another embodiment of the present invention can be made by a holder having a plurality of holes and a vessel having a concavity for accommodating the edge of the holder. Primers specific to the target DNA fragment species (specific primers), respectively, are immobilized on the inner surfaces of the holes, or they are placed in the holes separately on the basis of the kinds of the specific primers after being immobilized on beads. A free primer common to the target DNA fragment species (a common primer) is mobile in the vessel together with a solution and other reagents (reaction substrates and reagents necessary for PCR, such as enzymes).

When the holder having a plurality of holes is immersed in the reaction solution contained in the vessel, the reaction solution enters all the holes uniformly to be subjected to PCR. The use of immobilized primers (specific primers) specific to the DNA fragment species confines the PCR products in the holes. Therefore, by-products caused by the reactions between two or more kinds of the specific primers in the PCR are not produced.

As described above, according to the present invention, a plurality of DNA fragment species contained in each sample to be analyzed can be amplified by PCR under the same conditions at the same time, and the PCR products can be separated and recovered on the basis of the kinds of the target DNA fragment species.

By immobilizing the specific primers on the surfaces of solid supports such as separate fine particles, beads or fibers to separate them spatially from one another, the reaction area in the PCR can be restricted around the surface areas of the solid supports, and it is possible to prevent the production of undesired DNA products by the cross reaction among the specific primers.

Thus, the quantitative and comparative analysis for a plurality of target DNA fragment species in each sample to be analyzed becomes possible. Furthermore, the method of the present invention saves the labor of sample preparation and permits the reduction of reagents for PCR reaction.

The typical constitution of the present invention is outlined below with reference to FIG. 6.

A plurality of DNA fragment species to be amplified are present in a solution as a mixture. Reagents necessary for PCR, such as common primers (free primer), reaction substrates and enzymes are added into the aforesaid solution to obtain a reaction mixture. Primers specific to DNA fragment species (specific primers) to be amplified, respectively, are immobilized on beads, which are placed in the holes 301-1, ~, 301-9 of a holder 302 in distinction from one another on the basis of kinds of the specific primers.

Needless to say, the alternative way of holding specific primers is to immobilize them on the inner surfaces of the holes so as to be separately placed in different holes on the basis of the kinds of the specific primers.

When the holder having a plurality of the holes is immersed in the reaction mixture contained in a vessel, the reaction mixture containing all the target DNA fragment species, the reagent for reaction and the common primer goes into the holes. When PCR is carried out in each hole, the reaction conditions are the same in all the holes and the target DNA fragment species to be amplified are amplified by PCR in compartments, respectively, spatially separated on the basis of the kinds of the target DNA fragments.

The reaction solution can go in and out of the holes freely and the various target DNA fragment species can be amplified under the same conditions without mutual interaction, by the confinement of only the specific primer to the specific places. DNA fragments produced by the amplification in each hole can, of course, be separately collected and can be analyzed.

According to the present invention, mutual interaction of the primers can be avoided, target DNA fragment species in a plurality of samples can be amplified by PCR under the same conditions at the same time, and the PCR products can be separated and recovered on the basis of the kinds of the target DNA fragment species.

PREFERRED EMBODIMENTS

Fundamentally, the present invention is characterized in that the production of PCR by-products caused by interference or interaction undesired primers is prevented by using a free primer common to a plurality of target DNA fragment species (a common primer) and immobilized primers specific to the target DNA fragment species, respectively (specific primers), as primers for PCR amplification of various target DNA fragments, and by locating the specific primers in spatially and mutually isolated places. Furthermore, the PCR products can be easily and separately collected because they are in the mutually isolated places.

The present invention is explained below in detail with reference to the drawings.

A material (solid supports) for immobilizing primers specific to target DNA fragment species, respectively, includes the following materials such as fine particles or beads made of plastic, glass, ceramic or the like, magnetic fine particles, magnetic beads, etc., which can be discriminated as and divided into a plurality of groups based on their difference in physical or chemical properties. The first primers at a plurality of specific primer pairs capable of hybridizing specifically with the plurality of the DNA fragment species, respectively, is separately immobilized on the above-mentioned solid supports so as to be separated on the basis of the kinds of the specific primers.

The second primers of the plurality of species primer pairs are immobilized on the supports so as to collate to the kinds, respectively, of the supports. Target fragment of DNAs are hybridized with the primers, respectively, and immobilized on the supports and the complementary strands are synthesized. Each second primer is in a solution and is a common primer which hybridizes with at least two of a plurality of DNA fragment species produced by the immobilized primers. Simultaneous PCR of the plurality of the target DNA fragment species by the use of the first primers and the second primer is carried out. The products of the complementary strand synthesis or PCR can be separated and recovered on the basis of the kinds of the target DNA fragments of the DNA samples to be inspected, by monitoring the difference among the supports in the physical property. The kinds of the supports can be discriminated from one another by monitoring any of their specific weights, colors, degrees of magnetization, shapes, sizes and the like as the physical property.

As to the sizes of the fine particles or beads used here, their diameters are 0.5 $\mu$m to 500 $\mu$m.

Figure 1:
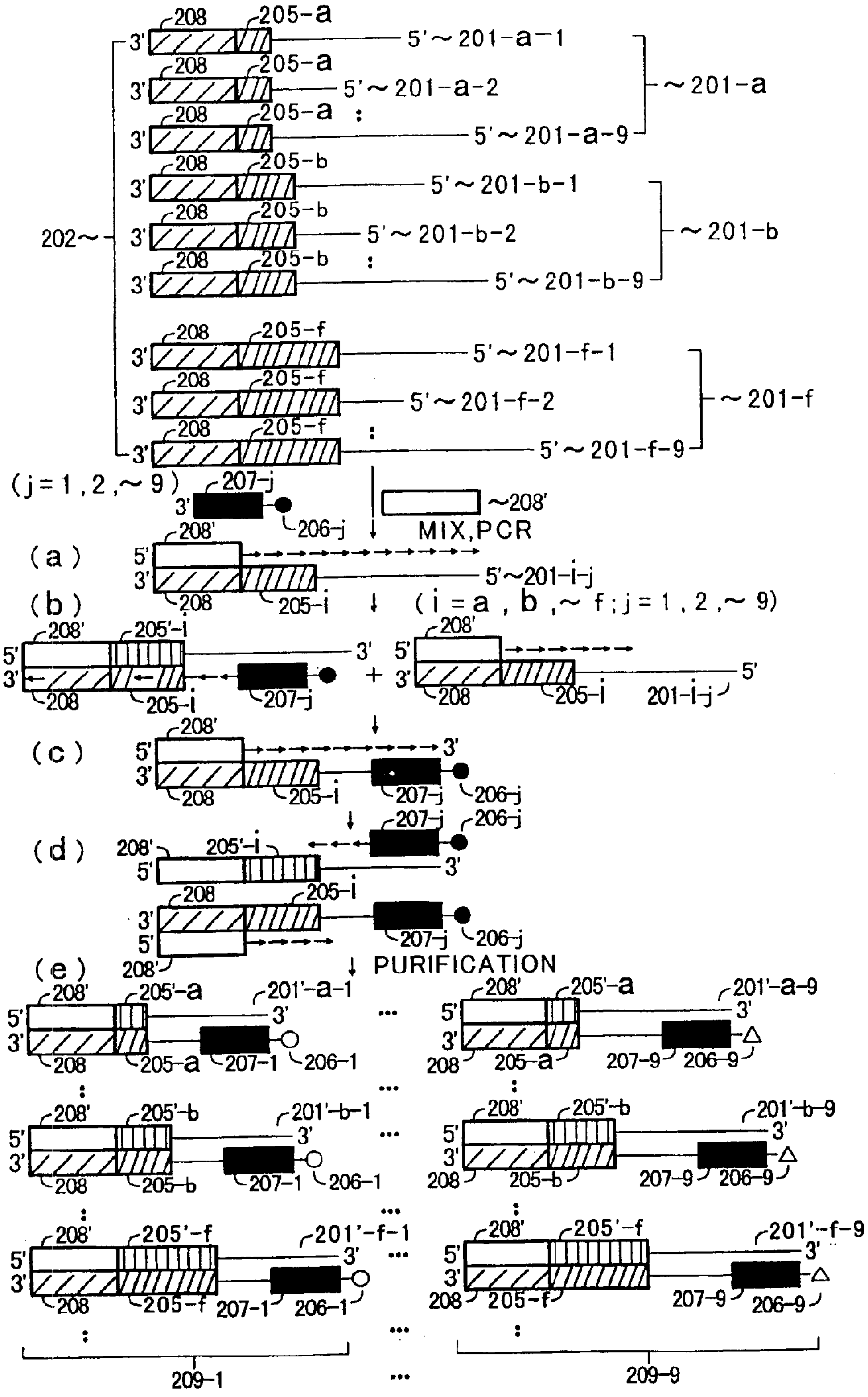
FIG. 1 is a diagram illustrating the sample preparation and the notations used in the figures. Here plural of DNA samples are notated with i (i=a–f) and plural species of target DNA fragments notated with j (j=1–9). The sequences of oligomers connected to the target DNA fragments have two parts common to all the target DNA fragments and specific parts which distinguish samples by their lengths. PCR amplification of fragments are carried out at the same time and under the same conditions in a vessel by using fine particles or beads, which are different in diameter and have primers specific to target DNA fragment species, respectively, on the surfaces.

A method for preparing samples to be subjected to PCR amplification is explained below. In the following explanation, as shown in FIG. 1, DNA samples for comparative analysis are denoted by 201-*i* (i=a, b, ~, f), and target DNA fragment species-j originated from the DNA sample 201-*i* are denoted by 201-*i*-*j* (i=a, b, ~, f; j=1, 2, ~, 9).

In each of the following examples, a plurality of target DNA fragment species (e.g., cDNA fragment species) 202 originated from a plurality of DNA samples are amplified by PCR and separated and collected on the basis of the kinds of the target DNA fragment species. In each of the following examples, the number of DNA samples is 6 and the number of target DNA fragment species is 9. Needless to say, the number of DNA samples and the number of target DNA fragment species are varied depending on a purpose of analysis.

In the base sequence of the target DNA, target regions to be amplified are determined, and primers (specific primer) 207-*j* (j=1, 2, ~, 9) are prepared to hybridize specifically with the base sequences (specific base sequences), respectively, of the target regions to be amplified. The DNA is cleared with restriction enzymes at the recognition sites present in each target regions. An oligomer having a known base sequence is bonded to the end of each of the digested DNA fragments by ligation. Each target region between the known base sequence originated in the bonded oligomer and the specific base sequence is subjected to PCR amplification to obtain samples for comparative analysis.

In the examples explained below with reference to FIG. 1, FIG. 2 and FIG. 3, "201-*i*-*j*" are used to represent the single stranded target DNAs having no oligomers with a known base sequence attached at the 5'-ends of the fragment. Needless to say, an oligomer having a known base sequence may be attached to the fragments.

Figure 2:
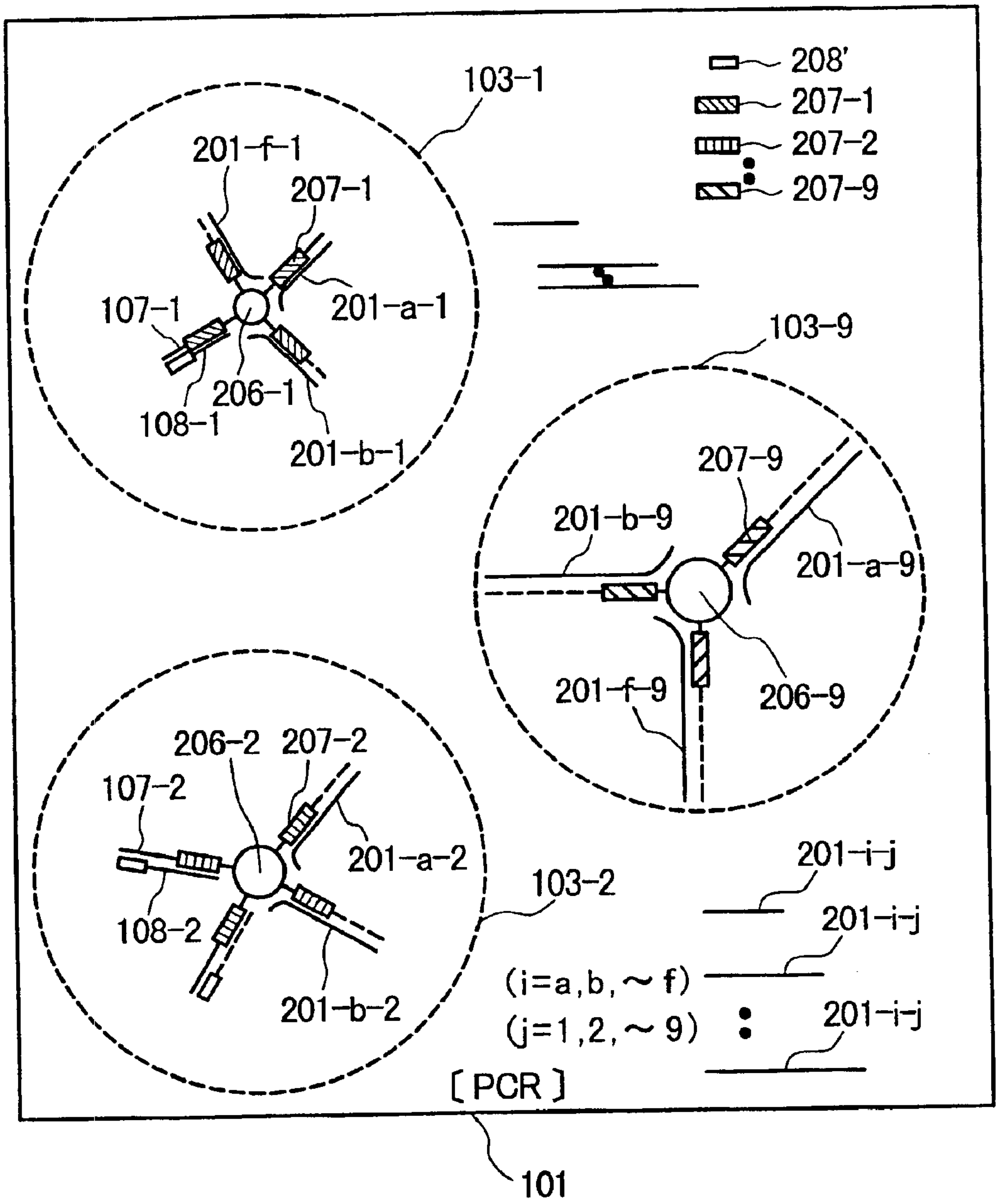
FIG. 2 is a diagram schematically showing simultaneous PCR amplification of the plurality of the target DNA fragment species by the use of the fine particles or beads, which are different in diameter and have specific primers, respectively, immobilized thereon, in Example 1 of the present invention.
Figure 3:
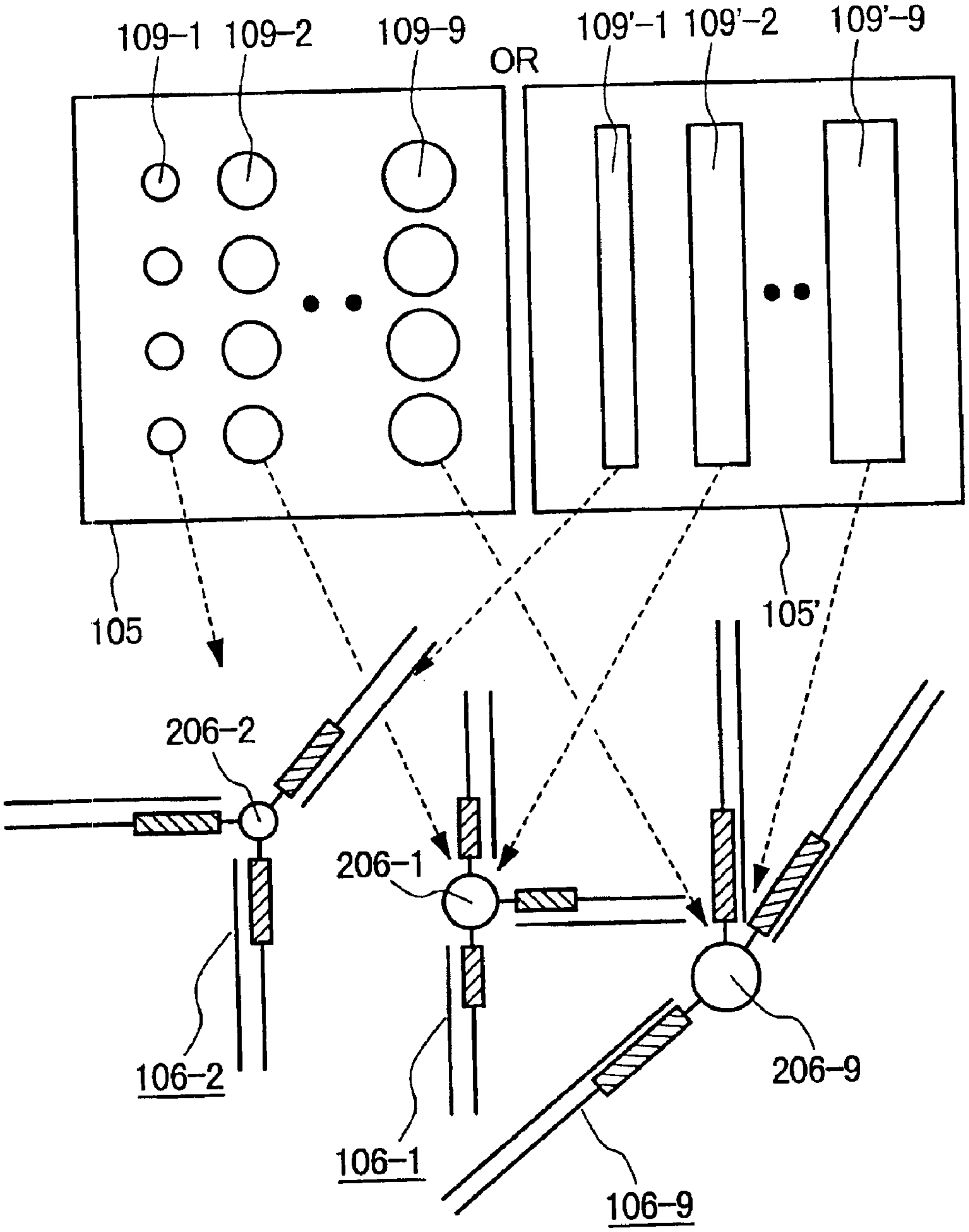
FIG. 3 is a diagram showing a method for separating and collecting a plurality of target DNA fragment species on the basis of their kinds by separately collecting the fine particles or beads on the basis of their sizes by the use of a sheet having holes or a sheet having slits, in Example 1 of the present invention.

The examples shown in FIG. 1, FIG. 2 and FIG. 3, are also applicable to double-stranded fragments and each region between the known base sequence and the specific base sequence can be subjected to PCR amplification in the same manner as above to obtain samples for comparative analysis.

The base sequence of the ligated oligomer having a known base sequence comprises a common base sequence 208 and a discriminating base sequence 205-*i* (i=a, b, ~, f) for discriminating the DNA samples, which follows the 5'-end of the common base sequence 208. The discriminating base sequence 205-*i* is a base sequence for discriminating target DNA fragments originated from the DNA sample-i by its length depending on the DNA samples.

That is, the length of the discriminating base sequence 205-*i* (i=a, b, ~, f) is the same for target DNA fragments 201-*i*-*j* (j=1, 2, ~, 9) in the sample-i (i=a, b, ~, f). The common base sequence 208 at the 3'-end of each of target DNA fragment species 201-*i*-*j* (j=1, 2, ~, 9) in the DNA sample-i (i=a, b, ~, f) is the same irrespective of the DNA sample and the DNA target fragment species. A free primer 208' for PCR amplification which is in a reaction solution hybridizes with the common base sequence 208.

The specific primers are immobilized at their 5'-end on the surfaces of separate solid supports such as fine particles or beads through linkers, respectively, so as to be separated on the basis of the kinds of the specific primers. Needless to say, a plurality of the specific primers of the same kind are immobilized on the surface of one solid support.

EXAMPLE 1

Example 1 is a case where different DNA probes (primers) are immobilized on different beads, respectively, and various target DNA fragments are amplified by PCR in distinction from one another, and the amplified products are held on the beads and then separately collected.

In Example 1, a method is explained which comprises immobilizing specific probes (specific primers) 207-*j* (j=1, 2, ~, 9) capable of hybridizing specifically with a plurality of target DNA fragment species 201-*i*-*j* (i=a, b, ~, f; j=1, 2, ~, 9), respectively, in each of a plurality of DNA sample-i (i=a, b, ~, f) on the surfaces of fine particles or beads 206-*j* (j=1, 2, ~, 9) having different diameters for the different target DNA fragment species; and dispersing the fine particles or beads in a reaction solution to carry out PCR amplification of the plurality of the target DNA fragment species 201-*i*-*j* (i=a, b, ~, f; j=1, 2, ~, 9) in each of the plurality of the DNA samples-i (i=a, b, ~, f) by using each of the specific primers 207-*j* (j=1, 2, ~, 9) and a common primer (a free primer) 208' capable of hybridizing with at least two of the plurality of the target DNA fragment species in common.

FIG. 1 is a diagram illustrating the sample preparation and the notations used in the figures. Here a plurality of DNA samples are notated with i (i=a–f) and a plurality of species of target DNA fragments in a sample are notated with j=1–9). The sequences of oligomers connected to the target DNA fragments have two parts, a part common to all target DNA fragments and a specific part which distinguish DNA samples by their lengths. PCR amplification of target DNA fragments are carried out at the same time and under the same conditions in a vessel by using fine particles or beads, which are different in a physical parameter such as diameter or color and have primers specific to target DNA fragment species, respectively on the surfaces.

FIG. 2 is a diagram schematically showing the simultaneous PCR amplification of the plurality of the target DNA fragment species in each of the plurality of the DNA samples, by the use of the fine particles or beads, which are different in diameter in this example and have the specific primers immobilized thereon, in Example 1.

First, the sample preparation method of the present invention shown in FIG. 1 is outlined below. FIG. 1 shows a case where 9 kinds of the target DNA fragments contained in DNA samples 201-*i* (i=a, b, ~, f) are amplified by PCR and the amplification products are separately collected.

Each of DNA samples to be analyzed is cleaved with restriction enzymes. An oligomer is bonded to the end of each of the cleaved fragments by ligation. The oligomer is composed of a common base sequence portion 208 which is the same for and common to all the target DNA fragments, and a discriminating base sequence 205-*i* (i=a, b, ~, f) which discriminates the DNA samples by their lengths.

As shown in FIG. 1, 9kinds (which may be increased or decreased but an explanation is given here by taking the case of 9 kinds) of target DNA fragments 202 (originated from the plurality of the DNA samples to be inspected) having various base sequences and lengths are produced for each of DNA samples. In FIG. 1, only single stranded DNA fragments each having the oligomer at the 3'-end are shown to simplify the procedure. In actual cases, the oligomers are ligated to double-stranded DNA fragments, from which single stranded DNA fragments are produced. The target DNA fragments used here are the single-stranded DNA fragments shown in FIG. 1.

PCR amplification is carried out by using a primer 208' having a base sequence complementary to the terminal base sequence 208 of each of the plurality of the DNA fragments 202, and specific primers 207-*j* capable of hybridizing specifically with the target DNA fragments, respectively. The specific primers 207-*j* are immobilized on different beads so as to be separated on the basis of the kinds of the specific primers 207-*i*, and hence are located in different places (beads), respectively, on the basis of the kinds of the specific primers 207-*i*.

Therefore, the PCR products are produced also in the mutually isolated places. In the first complementary-stand extension reaction, the common primer 208' hybridizes with a target DNA fragment to form a complementary strand ((a) in FIG. 1). The specific primer 207-*j* hybridizes with the formed complementary strand, and complementary-strand extension takes place ((b) in FIG. 1). Thereafter, as shown in (c) and (d) in FIG. 1, the sequence region between the common primer 208' and the specific primer 207-*j* (j=1, 18, 9) is amplified in the place only in which the specific primer is located ((e) in FIG. 1).

DNA fragments, which have different terminal base sequences (discriminating sequences 205-*i* (i=a, b, ~, f)), respectively, for the different samples-i (201-*i* (i=a, b, ~, f)) are obtained are increased while maintaining the relative abundances of the fragments as in the original DNA samples. Since the amplification is carried out at a localized area, the amplified DNA fragments can be separately collected on the basis of their kinds then utilized or analyzed.

The above is an outline of the sample preparation method of the present invention shown in FIG. 1. A detailed explanation is given below.

For separately collecting the PCR products by sorting, the specific primers 207-*j* are immobilized on the surfaces of the fine particles or beads 206-*j* having different diameters or colors, so as to be separated on the basis of the kinds of the specific primers 207-*j*. The fine particles or beads 206-*j* (j=1, 2, ~, 9) immobilizing the specific primers 207-*j* are placed together in a reaction vessel 101. A plurality of target DNA fragment species (cDNA fragments) 202 (including all target DNA fragment species 201-*i*-*j* (i=a, b, ~, f; j=1, 2, ~, 9) in the plurality of the DNA samples) and reagents necessary for PCR such as enzymes and reaction substrates are added and PCR is carried out.

As shown in (a) in FIG. 1, a strand complementary to the target DNA fragment species 201-*i*-*j* is produced by the extension reaction of the free primer 208' hybridized to the common base sequence 208 at the 3'-end of the target DNA fragment species 201-i-*j*. As shown in (b) in FIG. 1, a complementary strand is synthesized from a specific primer 207-*j* immobilized on each fine particle or bead 206-*j* after hybridizing to the complementary DNA strand produced by the common primer extension.

The specific primer 207-*j* is hybridized within an inherent base sequence portion 203-*j* (j=1, 2, ~, 9) (not shown) of the DNA strand complementary to the DNA fragment species 201-*i*-*j* in the sample i (or the 3'-end of the oligomer with a known base sequence attached to the 5'-end of the DNA fragment species 201-i-j) and the 3'-end of a base sequence 205'-*j* complementary to the discriminating sequence 205-*i*.

As a result, the specific primer 207-*j* immobilized on the surface of the fine particle or bead 206-*j* is extended to make a complementary strand. Since the different specific primers (probes) 207-*j* are immobilized on the different fine particles or beads 206-*j* having different physical properties such as diameters or colors, different DNA strands are produced on the different fine particles or beads 206-*j* having different physical properties such as diameters or colors.

As shown in (c) in FIG. 1, by the extension reaction of the primer 208' in solution, a strand complementary to the extended strand of the specific primer 207-*j* is produced.

As shown in FIG. 2, the common probe 208' is hybridized with each of the DNA strands 107-1 and 107-2 extended from the specific primers, respectively, immobilized on the surfaces of the fine particles or beads, and the DNA strands 108-1 and 108-2 extended from the common probe are produced. As shown in (d) in FIG. 1, PCR amplification is carried out by utilizing the produced DNA strands.

The products obtained by the above reactions are double stranded DNA fragments as shown in (e) in FIG. 1. They are composed of a first single strand immobilized on the fine particle or bead 206-*j* and a second single strand being produced by the common primer extension and having a base sequence complementary to the first single strand. A first single strand has, at the 3'-end side, the common base sequence 208 and the discriminating base sequence 205-*i* subsequent thereto for discriminating the target DNA fragment species 201-*i*-*j* in the DNA sample 201-*i*, and has, at the 5'-end side, the base sequence of the specific primer 207-*j*. Thus, DNA copies derived from the target DNA fragment species 201-*i*-*j* (i=a, b, ~, f; j=1, 2, ~, 9) are obtained.

As a result, for each target DNA fragment species-j, DNA fragment groups 209-*j* containing copy DNA fragments 201'-*i*-*j* (i=a, b, ~, f), respectively, are obtained for every j (j=1, ~, 9).

In FIG. 1, the size of the fine particles or beads 206-*j* is indicated by the symbol ●, and for example, the size of 206-1 is indicated by the symbol ○, and the size of 206-9 by the symbol Δ. Of course, color coding of fine particles or beads can be used instead of size coding.

Complementary strands are synthesized by using the fragment groups 209-*j* obtained for the DNA fragment species-j, respectively, by replication, as templates and a fluorophore-labeled common primer 208' (capable of hybridizing with the common base sequence 208), and are electrophoresed. The electropherograms are compared so as to decide the presence ratio of the target fragment species 201-*i*-*j* (f ; j=1, 2, ~, 9)) in each of the plurality of DNA samples 201-*i* (i a, ~, f).

As shown in FIG. 2, the fine particles or beads are dispersed in a PCR solution, so that effective reaction regions 103-*j* (j=1, 2, ~, 9) around the beads 206-*j* holding the different specific primers 207-*j* are sufficiently apart from one another. Since a single strand released from each DNA double strand which is obtained as a complementary strand extension product, is present near the fine particle of bead, it hybridizes with a specific primer on the bead to do PCR amplification. The concentration of the complementary strand decreases with a distance from the fine particle or bead. As a result, undesired PCT products are hardly produced. To improve the efficiency, a substance having a high viscosity may be added to a reaction mixture to reduce the fragment mobility. Strands produced by amplification by the use of only the common probe 208' are preserved, but strands other than those trapped by the fine particles or beads are washed away after the reaction and hence have no actual undesirable influence.

The beads may occupy the different areas from one another so that the probes (primers) immobilized thereon may be separated on the basis of their kinds. As the different probes are on the different beads, respectively, and the beads are coded by different physical characteristics such as size or color, the beads are separated after the PCR by utilizing their characteristic (size or color), and then DNA fragments produced by the PCR amplification are separately collected.

FIG. 3 is a diagram showing a method for separating and collecting plurality of DNA fragment species on the basis of their kinds by separately collecting the fine particles or beads on the basis of their sizes by the use of a sheet having holes or a sheet having slits, in Example 1. The reaction solution is diluted with a solvent after PCR, and the fine particles or beads are separately collected on the basis of their sizes by the use of a sheet having holes or a sheet having slits while allowing the dilution to flow. The diameter of the holes 109-*j* (j=1, 2, ~, 9) for separating the fine particles or beads on the basis of their sizes, or the size of aperture of the slit 109-*j* (j=1, 2, ~, 9) for separating the fine particles or beads on the basis of their sizes is such that the fine particles or beads can pass through the holes or the slits.

The dilution of the reaction solution after PCR is passed through the holes 109'-*j* or the slits 109'-*j* while being allowed to flow from left to right on the sheet having holes or a sheet having slits, which is in an inclined state. Thus, fine-particle or bead fractions 106-*j* (j=1, 2, ~, 9) are obtained by the separation on the basis of the sizes. The DNA fragments 209-1, 209-2, ~, 209-9 as amplification products shown in FIG. 1 are separately collected as fractions 106-1, 106-2, ~, 106-9.

The diameter of the fine particles or beads shown in FIG. 2 increases in the order of the fine particles or beads 206-2, 206-1 (shown by the symbol ○ in FIG. 1), 206-3, ~, 206-9 (shown by the symbol Δ in FIG. 1).

Figure 4:
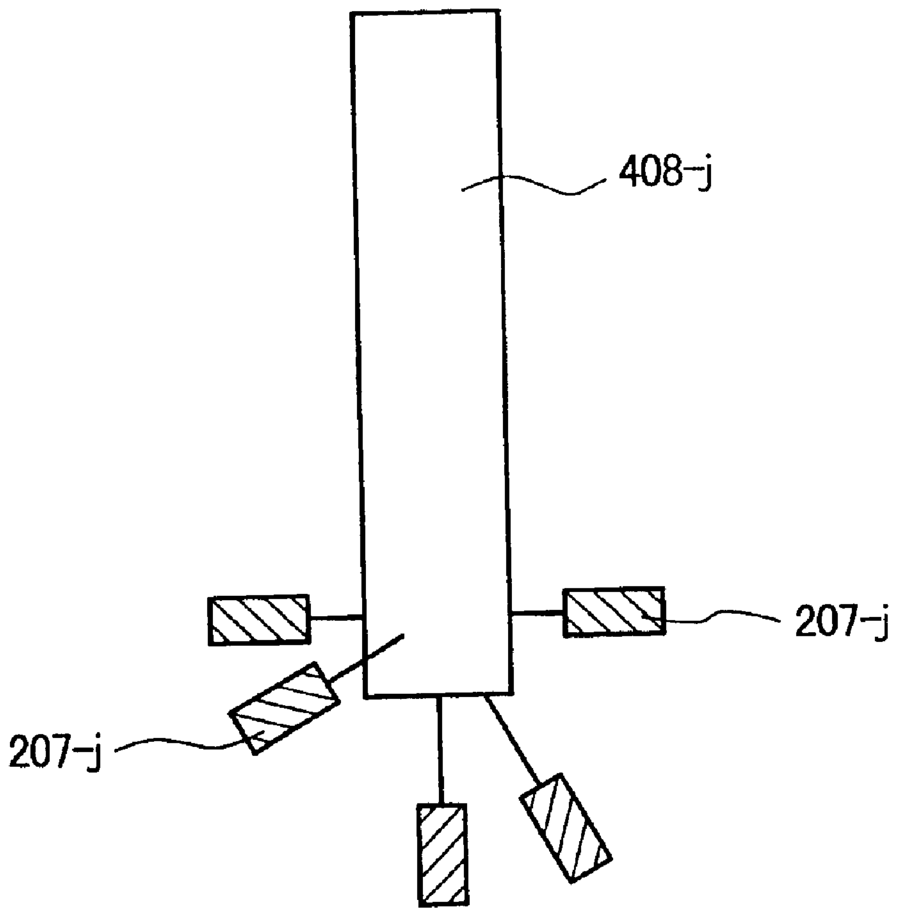
FIG. 4 is a diagram illustrating a method comprising immobilizing specific primers on the surfaces of fibers used in place of fine particles or beads, amplifying a plurality of target DNA fragment species by PCR at the same time, and separating and collecting the amplified products of the plurality of the target DNA fragment species on the basis of their kinds, in Example 1 of the present invention.

FIG. 4 is a diagram illustrating a method of using fibers to immobilize specific primers on the surfaces. In the structure shown in FIG. 4, specific primers 207-*j* (j=1, 2, ~, 9) are immobilized on the surfaces of different fibers 408-*j* (j=1, 2, ~, 9) so as to be separated on the basis of their kinds.

The fibers 408-*j* are immersed in a reaction solution in the reaction vessel 101 shown in FIG. 2, and PCR is carried out. The specific primer 207-*j* is immobilized on the surface at or near the end of the fiber 408-*j*. The fibers are made of plastic or glass. In general, thin thread-like pieces may be used in place of the fibers. As the thin pieces, any pieces may be used they can be discriminated from one another on the basis of any of appearance (external shape), color and dimensions such as thickness and length. Thread-like pieces such as fibers can easily be handled and hence permit easy separation and recovery of PCR products.

Complementary strands are synthesized by using the separated and recovered PCR products, as templates for the comparative analysis of sample. The fluorophore-labeled hybridize with the templates primers, respectively, then are electrophoresed. The resulted electrophoretic patterns are compared, to determine the presence ratio of the noted fragment species in each of the plurality of DNA samples.

EXAMPLE 2

In Example 1, the fine particles or beads (or the fibers) are placed together in one reaction vessel irrespective of the kinds of the immobilized specific primers. In Example 2, a capillary is used as a reaction vessel, fine particles or beads are held in the capillary so as to be located in different places on the basis of the kinds of specific primers (probes) immobilized on the surfaces of the fine particles or beads, and PCR is carried out by the use of the specific primers spatially separated on the basis of their kinds.

In this method, mutual interference by specific primers is prevented and the PCR products are present only in the vicinity of the fine particles or beads immobilizing the corresponding specific primers. Therefore, efficient multi-component PCR can be carried out.

Figure 5:
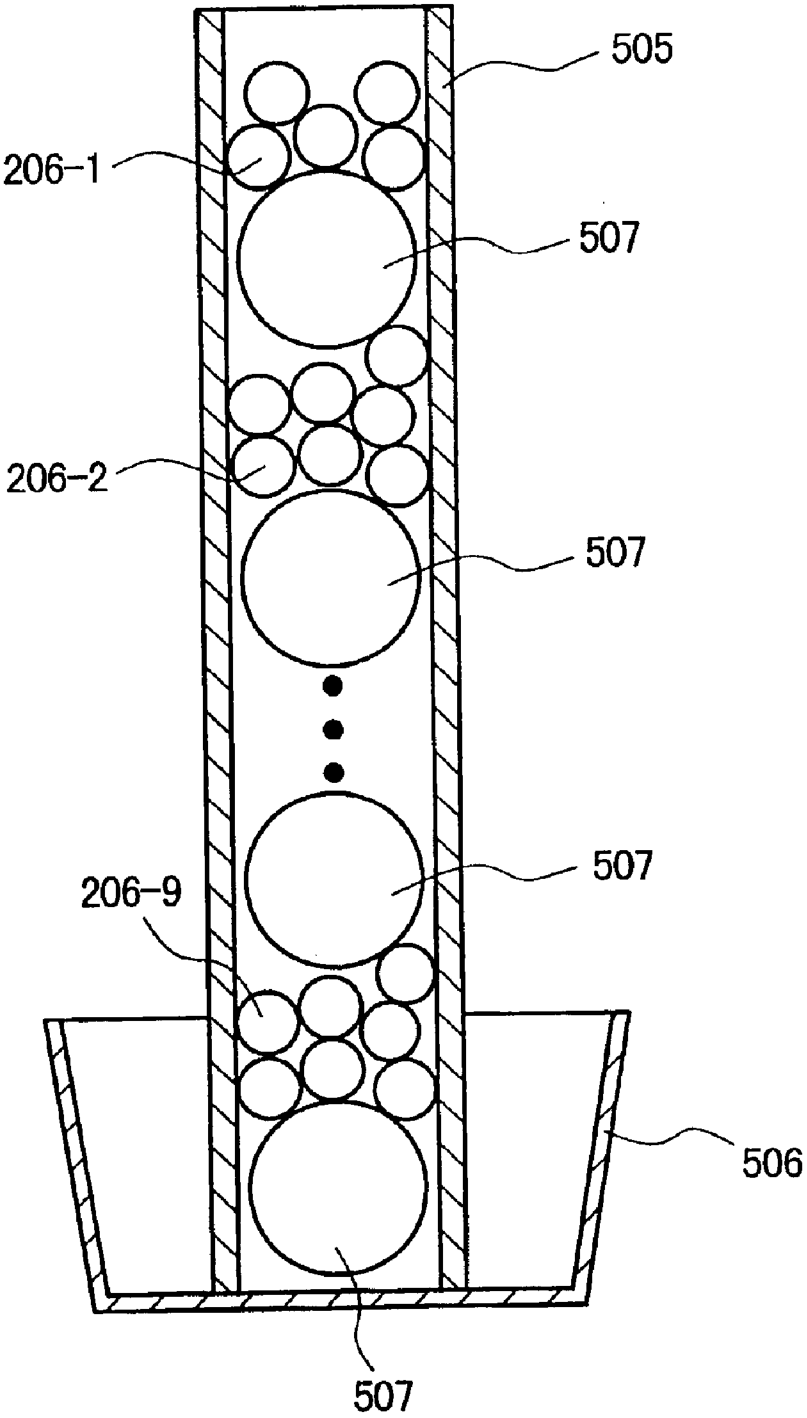
FIG. 5 is a diagram showing a structure for carrying out simultaneous PCR of a plurality of target DNA fragment species in a capillary by holding fine particles or beads, which have specific primers immobilized thereon, in the capillary so as to locate the fine particles or beads in different compartments on the basis of the kinds of the specific primers, in Example 2 of the present invention.

FIG. 5 is a diagram illustrating Example 2. In Example 2, fine particles or beads immobilizing specific primers are held in a capillary so as to be located in different places on the basis of the kinds of the specific primers. In the capillary, simultaneous PCR of a plurality of target DNA fragment species is carried out.

As shown in FIG. 5, fine particles or beads 206-*j* (j=1, 2, ~, 9) are packed in a capillary 505 having an inside diameter of 220 μm, so that each group thereof may be isolated by dummy fine particles or beads. For different j values, different specific primers 207-*j* (not shown) are immobilized on the fine particles or beads 206-*j*.

The specific primers are separated by the dummy fine particles or beads 507 on the basis of the kinds of the specific primers. Since fine particles or beads of 200 μm are used as the dummy fine particles or beads 507, a group of the fine particles or beads 206-*i* immobilizing the specific probes does not pass through the region filled with the dummy fine particles or beads 507 to mix with another group.

The bottom of the capillary 505 is held in a capillary-holding vessel 506 through a membrane (not shown) having holes with a diameter of about 150 um and PCR amplification is carried out by placing template DNAs and a PCR solution containing a common primer, in the capillary 505.

Since the PCR products are present only in areas in the capillary in which the corresponding fine particles or beads are present, efficient PCR amplifications are carried out in separate spaces, respectively. The PCR products can be taken out of the capillary in order for analysis.

The PCR products taken out separately in order and recovered are electrophoresed in the same manner as in Example 1. Thus, the relative abundance of presence ratios among the target fragments in each of a plurality of DNA samples can be obtained.

Needless to say, after removing the excess reagents while holding the PCR products in an optically transparent capillary used as the above-mentioned capillary, the relative abundance or presence ratio among the noted fragments in each of the plurality of the sample may be analyzed in the transparent capillary. This is just a probe array using a capillary containing fine particles or beads having probes.

EXAMPLE 3

Example 3 is a method in which fine particles or beads, which have specific probes immobilized on their surfaces, are placed in the cells (hole-like reaction portions) of a holder 302 mutually isolated so as to separate the fine particles or beads on the basis of their kinds, and a mixture of a reaction solution and template DNAs are fed as a common reaction solution from a reaction-solution-holding plate 303. The common reaction solution can pass through the cells.

Figure 6:
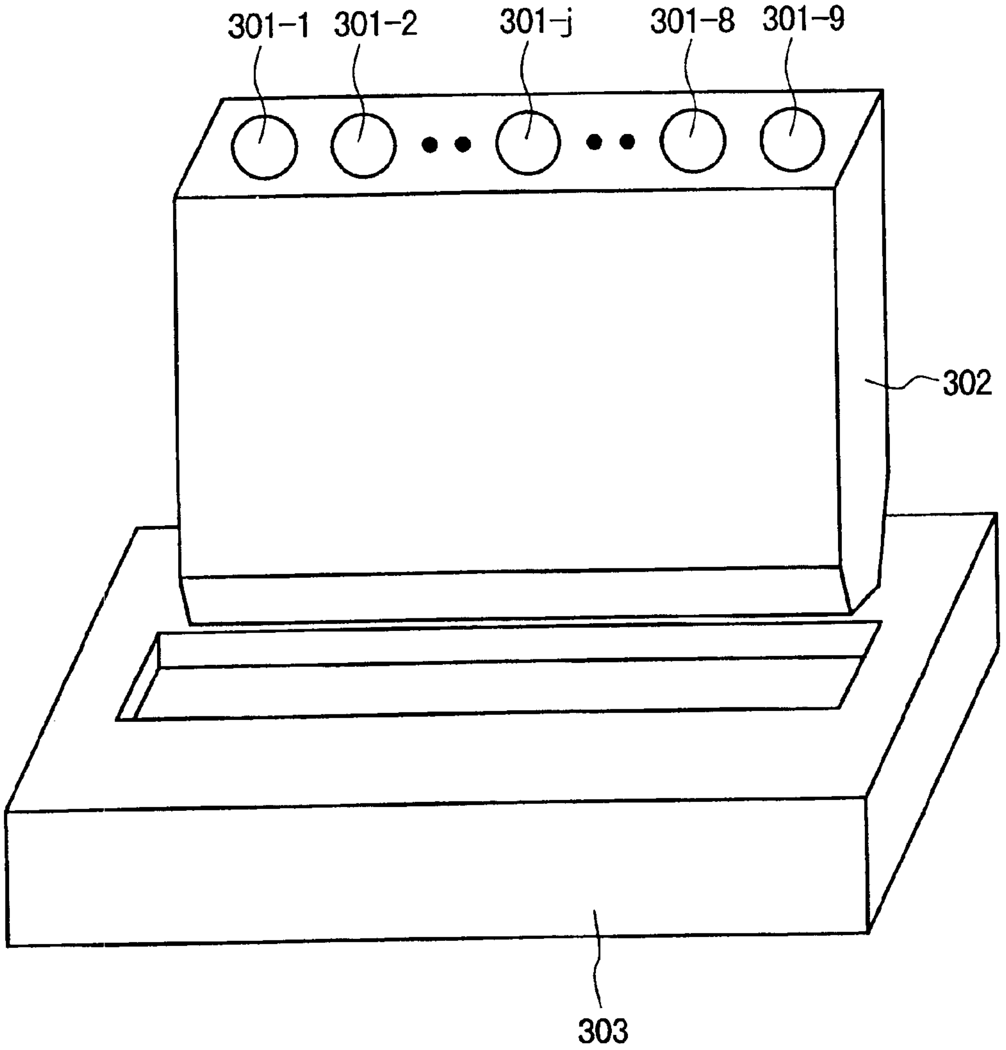
FIG. 6 is a perspective view showing the structure of a reaction device using a plate having hole-like reaction portion array for holding specific probes so as to separate them on the basis of their kinds, in Example 3 of the present invention.

FIG. 6 is a perspective view showing the structure of a reaction device having lineary arrayed holes as reaction portions for holding specific probes so as to separate them on the basis of their kinds, in Example 3. In the reaction device shown in FIG. 6, specific primers which have sequences complementary to a plurality of target DNA fragment species to be amplified, respectively, and hybridize specifically with the target DNA fragment species, respectively, are held in the holes of a holder 302 having a plurality of through-holes 301-1, ~, 301-9, so as to be separated on the basis of the kinds of specific primers.

A plurality of DNA fragment species and a PCR solution containing a common primer capable of hybridizing with the part of an oligonucleotide introduced into each DNA fragment species are accommodated in the concavity of a reaction-solution holding plate 303 having the concavity for receiving at least one edge of the holder. The PCR amplification of the target DNA fragment species is carried out inside the holes by the use of each specific primer and the common primer, whereby PCR amplification products are produced for each DNA fragment species in the corresponding hole.

The reaction device is composed of the holder 302 having hole-like reaction portion 301-*j* (j=1, 2, ~, 9) for holding specific probes 207-*j*, and the reaction-solution-holding plate 303 having a well or wedge-shaped concavity which accommodates template DNAs and a PCR solution containing a common primer and into which the lower and side tapered portion of the holder 302 can be inserted. The holder 302 is a thin plate having hole-like reaction portions 301-*j* having an inside diameter of hole of 0.2 mm. The holes 301-*j* having an inside diameter of 0.2 mm penetrate the holder 302.

In the example of structure shown in FIG. 6, a thin plate having a thickness of 0.5 mm, a height of 4 mm and a lateral length of 16 mm is used. The holes having an inside diameter of 0.2 mm are made at intervals of 0.1 mm. In the example shown in FIG. 6, the number of the holes is 9, but it can, of course, be increased. The reaction solution accommodated in the concavity of the reaction-solution-holding plate 303 is fed into each hole-like reaction portion 301-*j* from the lower part of the reaction portion when the lower and side tapered portion of the holder 302 is inserted into the well or wedge-shaped concavity of the reaction-solution holding plate 303.

As a result, only specific DNA fragment species are selectively amplified in the holes, respectively. The volume of the reaction solution fed into the well or wedge-shaped concavity of the reaction-solution-holding plate 303, is very small as 20 uL (microliter). Since this volume is the same amount as used for one conventional PCR, the amount of reagents used for one reaction in the multiple PCR can be reduced to about one-twelfth of that used in the conventional PCR. A method for holding specific probes in the hole-like reaction portions so as to separate them on the basis of their kinds is concretely explained below.

Figure 7:
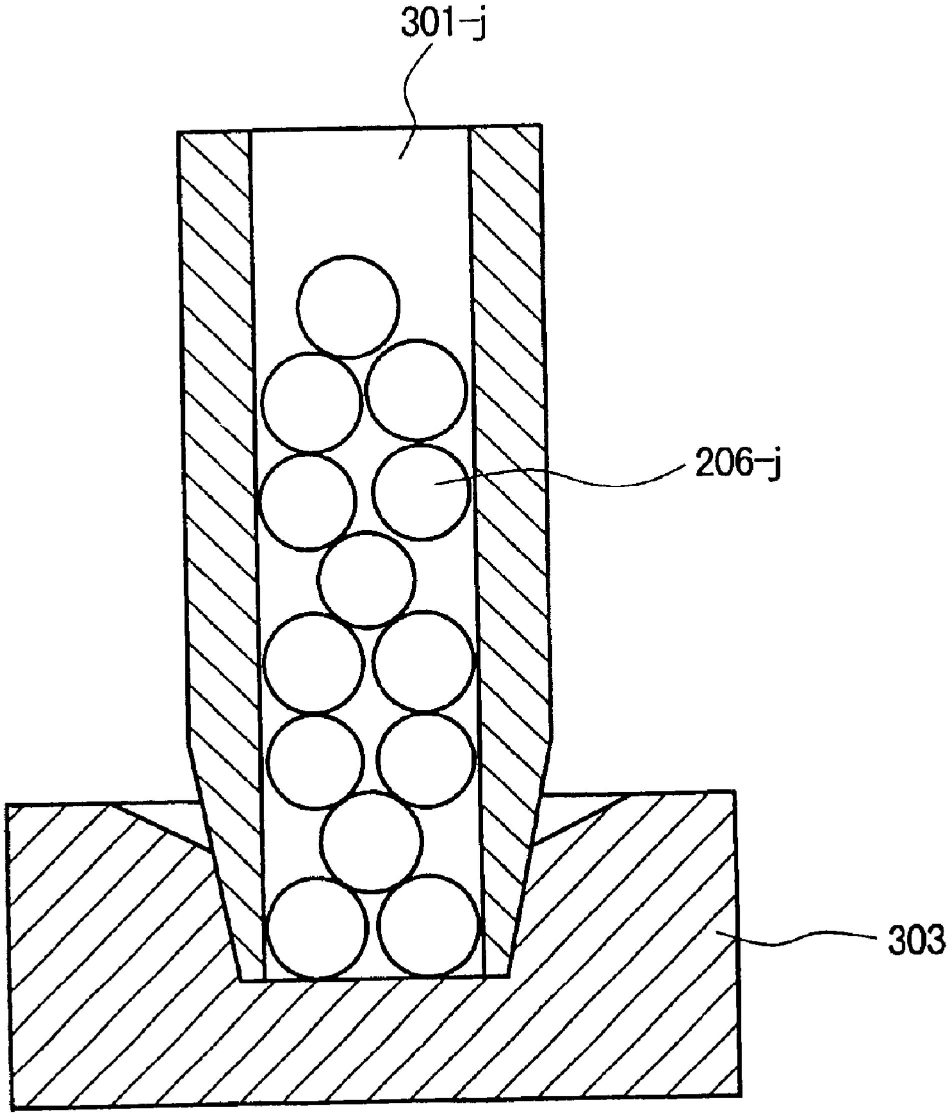
FIG. 7 is a cross-sectional view showing a way of keeping fine particles or beads, which have specific probes immobilized thereon, in the hole-like reaction portions of the strip-form array shown in FIG. 6 in the present invention, so as to assign the fine particles or beads to the kinds, respectively, of the specific probes.
Figure 8:
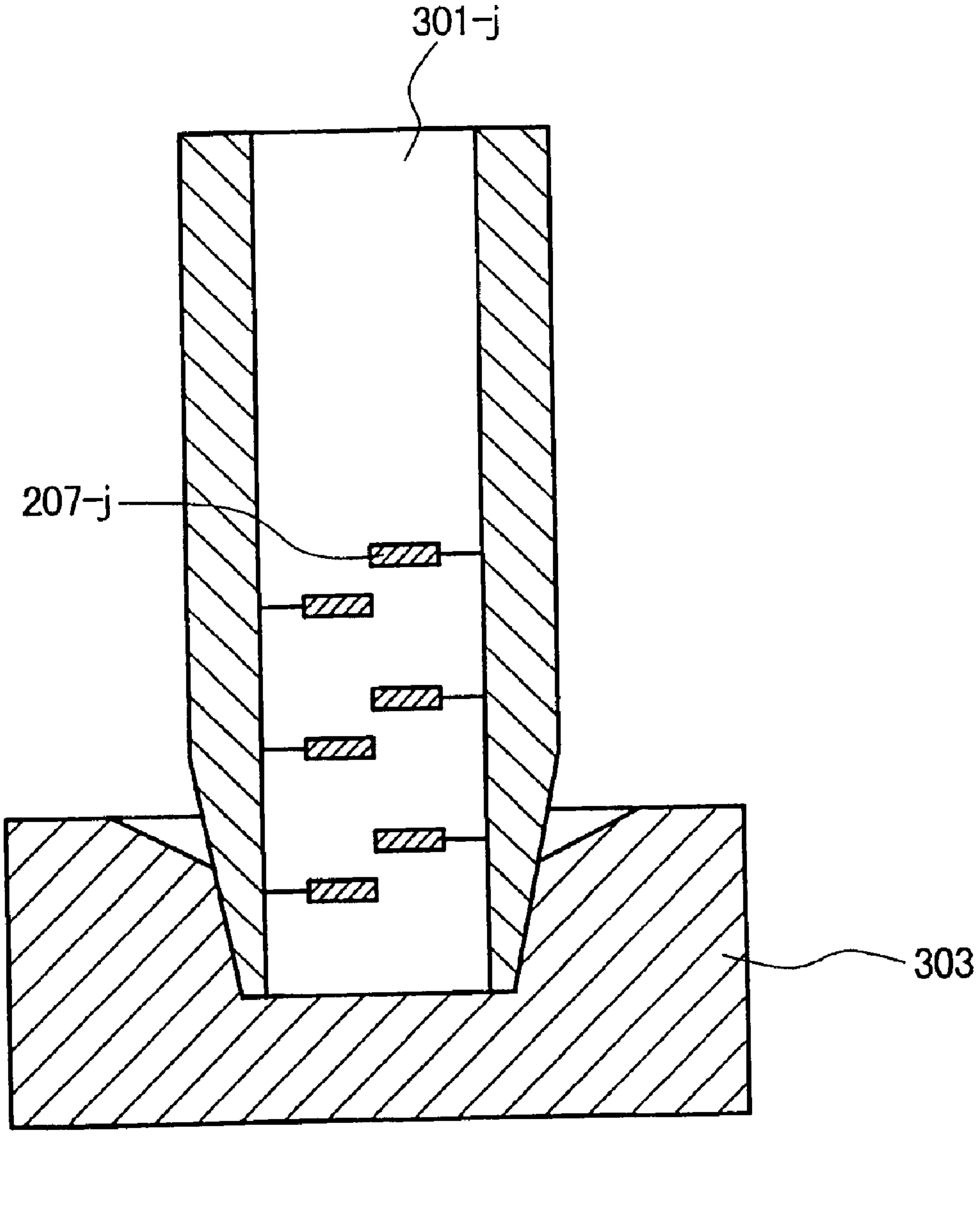
FIG. 8 is a cross-sectional view showing a structure for immobilizing specific probes on the inner 5 surface of each reaction portion of the plate having hole array shown in FIG. 6 in the present invention, so as to separate the specific probes on the basis of their kinds.
Figure 9:
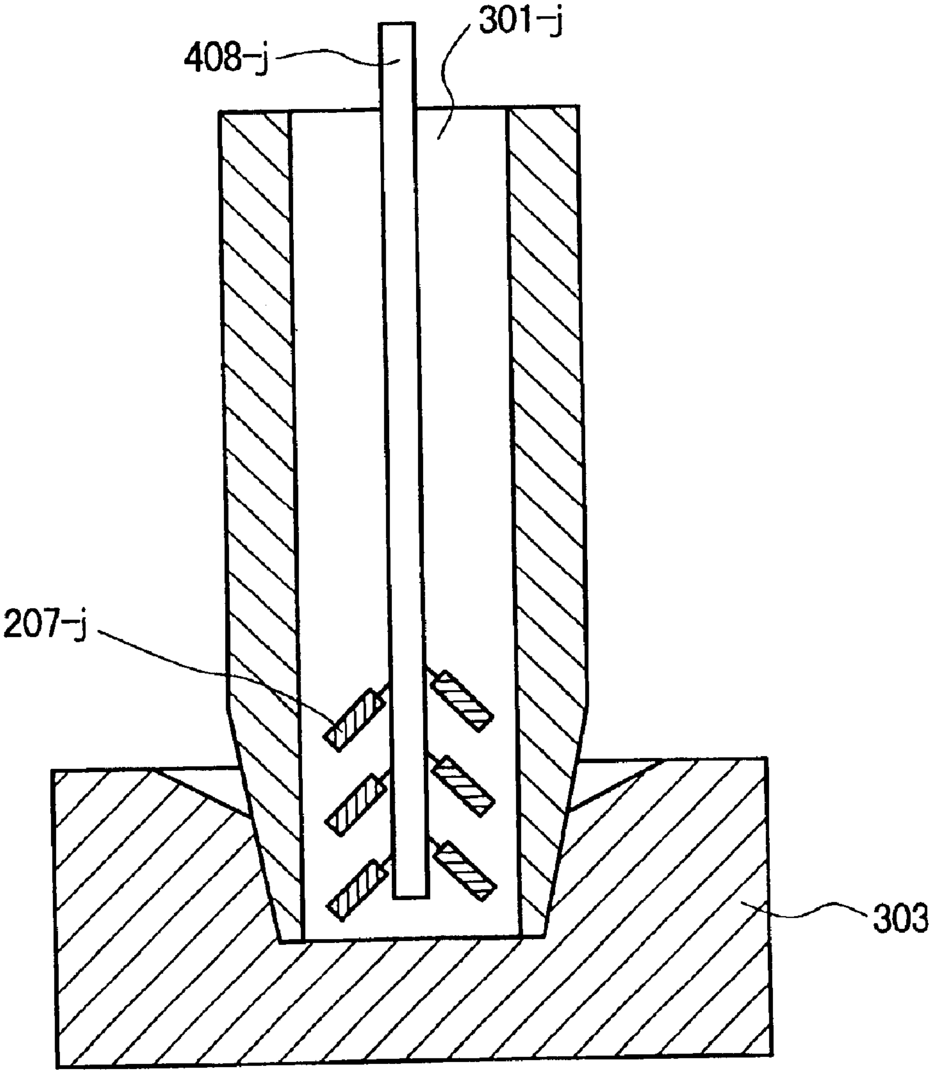
FIG. 9 is a cross-sectional view showing a way of keeping fibers immobilizing specific probes, in the hole-like reaction portions, respectively, shown in FIG. 6 in the present invention, so as to assign the fibers to the kinds, respectively, of the specific probes.

FIG. 7 is a cross-sectional view showing a structure for accommodating fine particles or beads, which have specific probes immobilized thereon, in the hole-like reaction portions (the holder 302) shown in FIG. 6, so as to separate the fine particles or beads on the basis of the kinds of the specific probes. FIG. 8 is a cross-sectional view showing a structure for immobilizing specific probes on the inner surfaces of the reaction portions of the holder 302 shown in FIG. 6, so as to separate the specific probes on the basis of their kinds. FIG. 9 is a cross-sectional view showing a structure for accommodating fibers immobilizing specific probes, in the hole-like reaction portions of the holder 302 shown in FIG. 6, so as to separate the fibers on the basis of the kinds of the specific probes.

In the structure shown in FIG. 7, fine particles or beads 206-*j* immobilizing specific probes 207-*j* (not shown) are accommodated in the hole-like reaction portions 301-*j* so as to be separated on the basis of the kinds of the specific probes 207-*j* (j=1, 2, ~, 9 in Example 3). In the structure shown in FIG. 7, the diameters of the fine particles or beads 206-*j* may be uniform irrespective of j (needless to say, they may be different depending on j).

In the structure shown in FIG. 7, fine 15 particles or beads 206-*j* immobilizing specific probes 207-*j* (not shown) which are different depending on j (j =1, 2, ~, 9 in Example 3) may be accommodated in the same hole-like reaction portion 301-*j* so as to be separated on the basis of the kinds of the specific primers by dummy fine particles or beads 507 as in the structure shown in FIG. 5. The bottom of the holder 302 is set on the reaction-solution-holding plate 303 through a membrane (not shown) having holes which does not permit the fine particles or beads 206-*j* to pass through.

In the structure shown in FIG. 8, specific probes 207-*j* are immobilized on the inner surfaces of the hole-like reaction portions 301-*j* so as to be separated on the basis of their kinds (j=1, 2, ~, 9 in Example 3). In the structure shown in FIG. 9, fibers 408-*j* immobilizing specific probes 207-*j* are accommodated in the hole-like reaction portions so as to be separated on the basis of the kinds of the specific probes 207-*j* (j=1, 2, ~, 9 in Example 3).

The inside diameter of the hole of each hole like reaction portion 301-*j* is larger than that of capillaries used for capillary electrophoresis. Complementary strands are amplified then synthesized in each holelike reaction portion 301-*j*. During the synthesis, the PCR products are used as templates and fluorophore-labeled primer complementary to the specific probes 207-*j*, respectively. Then, the complementary strands are introduced into capillaries for electrophoresis (see FIG. 12) and subjected to capillary electrophoresis. By comparing the electrophoretic patterns, the presence ratio among the target fragment species in each of a plurality of samples can be obtained.

In the structures shown in FIGS. 6 to 9 which are described above, the hole-like reaction portions are one-dimensionally located, though they can, of course, be two-dimensionally located by changing the sizes of the holder 302 and the reaction-solution-holding plate 303. These locations are characterized in that a reaction solution is held in one lot by the reaction solution-holding plate 303, and that the reaction cells (the hole-like reaction portions 301-*j*) are connected. Thus, the locations of the reaction cells are different from the locations of the lots where a reaction solution is held. Example 3 is advantageous also because that the dispensation of a reaction solution into the reaction cells is conducted automatically via the connection between the cells and the lots.

EXAMPLE 4

Figure 10:
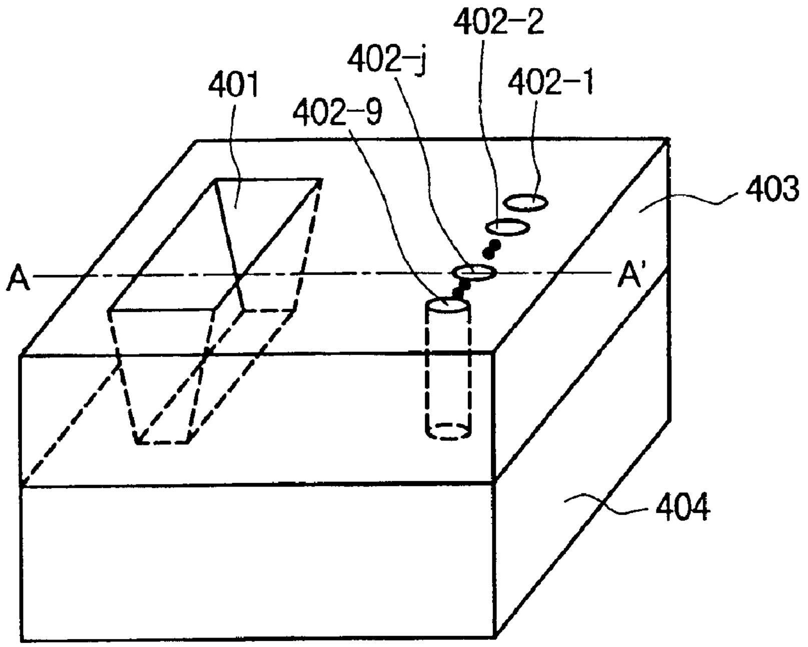
FIG. 10 is a perspective view showing the structure of a reaction device using a grooved plate in which specific probes are held so as to be separated on the basis of their kinds, in Example 4 of the present invention.
Figure 11:
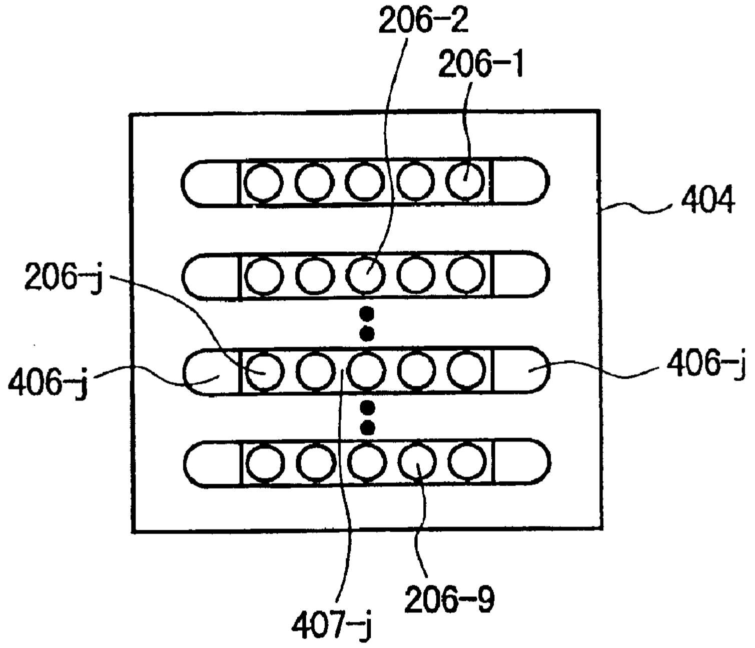
FIG. 11 is a plan view of the grooved plate that constitutes the reaction device shown in FIG. 10 in the present invention.
Figure 12:
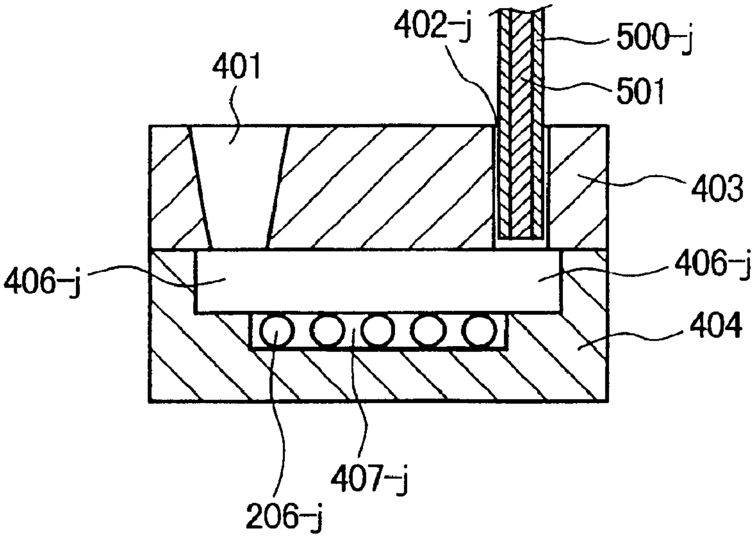
FIG. 12 is a cross-sectional view taken along the line A–A' of FIG. 10.

FIG. 10 is a perspective view showing the structure of a reaction device using a grooved plate in which specific probes are held so as to be separated on the basis of their kinds, in Example 4. FIG. 11 is a plan view of the grooved plate 404 that constitutes the reaction device shown in FIG. 10. FIG. 12 is a cross sectional view taken along the line A–A' of FIG. 10.

The reaction device shown in FIG. 10 is composed of reaction portions 407-*j* (j==1, 2, ~, 9) which hold fine particles or beads 206-*j* (j=1, 2, ~, 9) immobilizing specific probes 207-*j* (j=1, 2, ~, 9); a grooved plate 404 having fine grooves for solution flow 406-*j* (j=1, 2, ~, 9); a reaction solution vessel 401 into which template DNAs and a PCR solution containing a common primer are introduced; and an upper plate 403 having reaction solution outlets 402-*j* (j=1, 2, ~, 9) for discharging liquids containing PCR products.

Each of a combination of the reaction portion 407-*j* and the grooves for solution flow 406-*j* is composed of one continuous groove having different depths, and the reaction portion 407-*j* is composed of a groove deeper than the grooves for solution flow 406-*j*. The shallower groove for solution flow 406-*j* on one side communicates with the reaction solution vessel 401, and the shallower groove for solution flow 406-*j* on the other side connected to the reaction solution outlet 402-*j*.

Each of the reaction portions 407-*j*, the grooves for solution flow 406-*j*, the reaction solution outlets 402-*j* and the reaction solution vessel 401 is formed at each of two flat plates, by a micro-fabrication technique. The inner diameter of a pore constituting each reaction solution outlet 402-*j* is larger than that of capillaries 500-*j* (j==1, 2, ~, 9) packed with a electrophoresis medium 501 used for capillary electrophoresis.

After PCR, a mixture of the specific probes 207-*j* (j=1, 2, ~, 9) is placed in the reaction solution vessel 401, and complementary strands are synthesized in each reaction portion 407-*j* by using the PCR products as templates and fluorophore-labeled primers, respectively. Then, the complementary strands are introduced into capillaries for electrophoresis (see FIG. 12) and subjected to capillary electrophoresis. By comparing the electrophoretic patterns, the presence ratio among the target fragment species in each of a plurality of DNA samples can be known.

EXAMPLE 5

Figure 13:
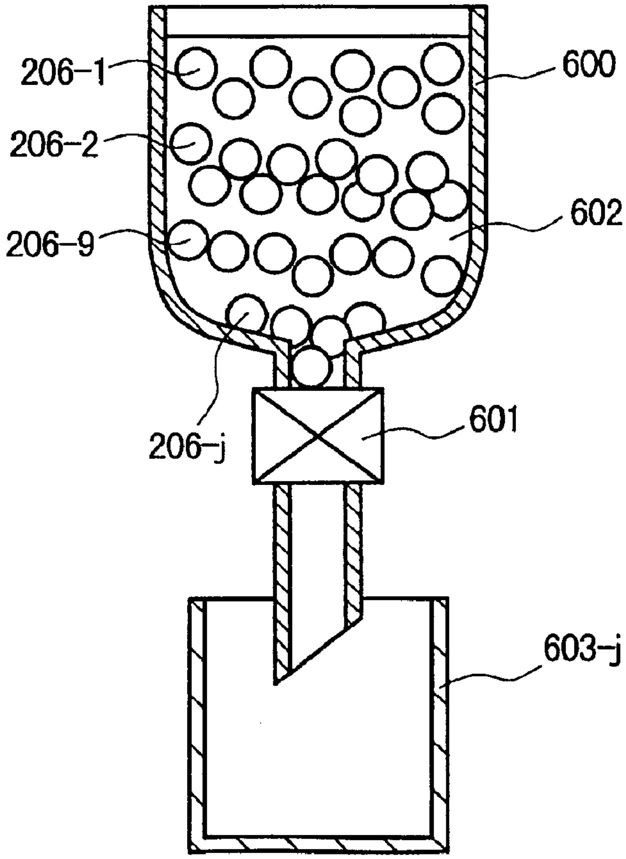
FIG. 13 is a cross-sectional view illustrating a structure for separating fine particles or beads on the basis of their specific gravity in Example 5 of the present invention.

FIG. 13 is a cross-sectional view illustrating a structure for separating fine particles or beads on the basis of their specific gravity in Example 5. Although the fine particles or beads are separated on the basis of their sizes in Example 1, it is possible to use plastic fine particles or plastic beads, which have been given different specific weights by the incorporation of a metal, and separate them on the basis of the specific weights.

In detail, specific primers are immobilized on plastic fine particles or plastic beads, which have the same diameter but have different specific weights, so as to correspond to the specific weights, respectively, of the plastic fine particles or plastic beads, and the fine particles or beads are separated and recovered by the detection of the specific gravity difference, among PCR products obtained by applying Example 1, whereby the PCR products are separated and recovered on the basis of the kinds of noted DNA fragments.

When the specific gravity of a solution containing the PCR products is gradually reduced, for example, by changing the salt concentration in the solution, the fine particles or beads can be separately collected in order of decreasing specific gravity. Example 1 is carried out in a transparent reaction vessel 600 equipped with a cock, by the use of fine particles or beads, which are different in specific gravity. After completion of PCR, the specific gravity of a solution 602 containing PCR amplification products is gradually reduced by changing the salt concentration in the solution 602. By combining the opening and shutting of the on-off cock 601 with the change of the salt concentration in the solution 602, the fine particles or beads can be separately collected in order of decreasing specific gravity to be recovered into different vessels 603-*j* (j=1, 2, ~, 9) so as to be separated on the basis of the specific weights of the fine particles or beads.

The PCR amplification products separated and recovered are electrophoresed in the same manner as in Example 1, whereby the presence ratio among the noted fragment species in each of a plurality of samples can be determined.

EXAMPLE 6

Figure 14:
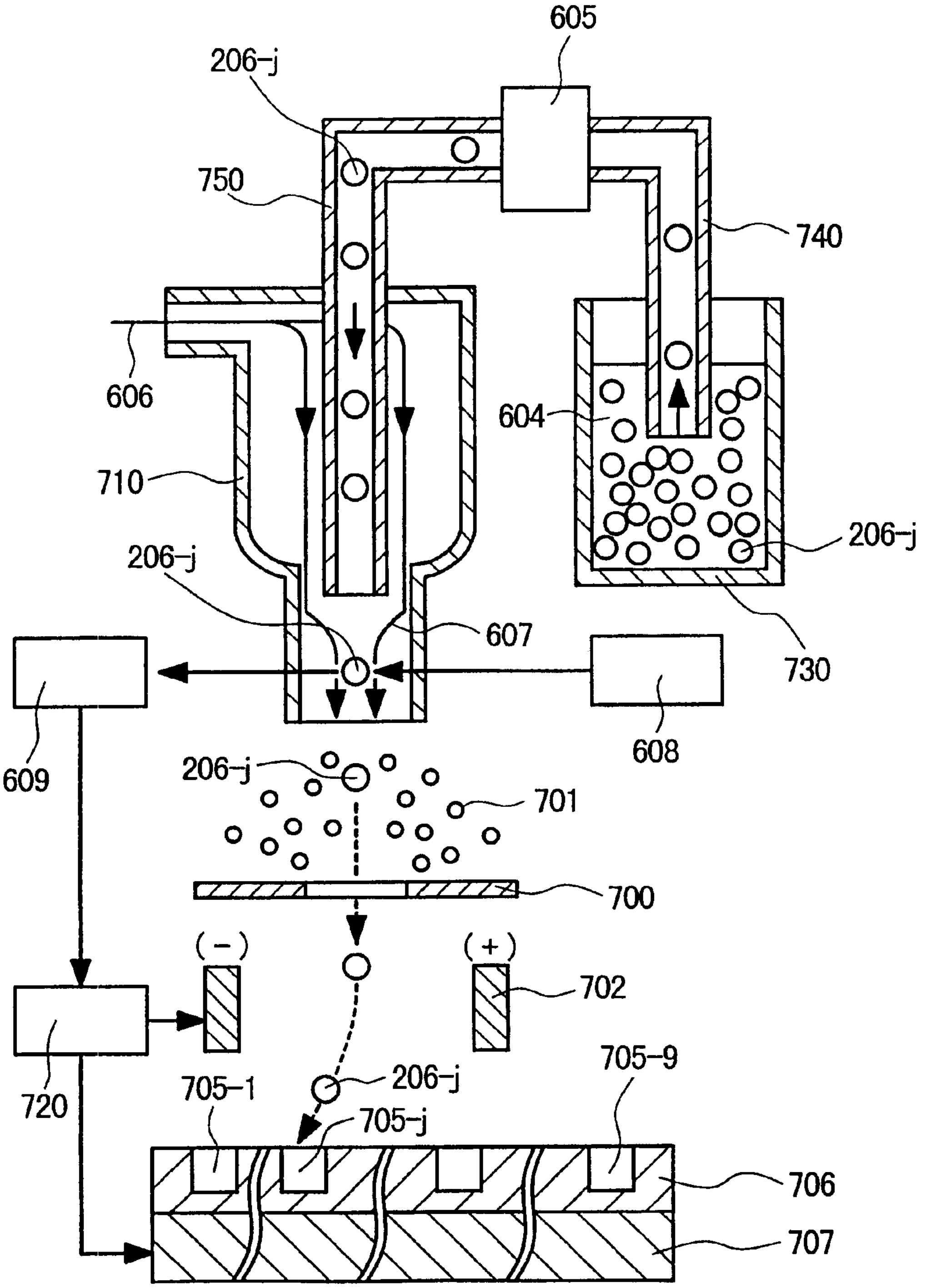
FIG. 14 is cross-sectional view illustrating a structure for separating fine particles or beads by optical discrimination among the colors of the fine particles or beads in Example 6 of the present invention.

FIG. 14 is cross-sectional view illustrating a structure for separating fine particles or beads by optical discrimination among the colors of the fine particles or beads in Example 6. Although the fine particles or beads are separated on the basis of their sizes in Example 1, it is possible to use fine particles or beads, which have been made optically discriminable by giving various colors thereto, and separate the fine particles or beads by detecting the difference in color among the fine particles or beads.

In detail, specific primers are immobilized on plastic fine particles or plastic beads, which have the same diameter but have different colors, so as to correspond to the colors, respectively, of the plastic fine particles or plastic beads, and PCR products produced from each target DNA fragment species are separated and recovered from PCR products obtained by applying Example 1, by utilizing the difference in color among the fine particles or beads, whereby the PCR products are separated and recovered on the basis of the kinds of noted DNA fragments. The fine particles or beads to be separated are accommodated in a vessel 703 as a mixture.

The fine particle or beads 206-*j* (j=1, 2, ~, 9) and a solution 604 containing PCR amplification products are sucked into an aspirating fine tube 740 at a constant rate by means of an aspirating and flowing pump 605 to be introduced into a flowing fine tube 750 at a constant rate. The fine tube 750 is connected to a sheath flow cell 710 into which a buffer solution 606 flows and in which a sheath flow 607 is formed. The fine particles or beads 206-*j* are released in the sheath flow 607.

The fine particles or beads 206-*j* flow together with the buffer solution in a capillary constituting the outlet of the sheath flow cell 710, while keeping a space between fine particles or beads. In the vicinity of the end of the capillary constituting the outlet of the sheath flow cell 710, the fine particles or beads 206-*j* are irradiated with laser beams from a laser beam source 608, and either light reflected from the fine particle or bead 206-*j* which passes the laser beam irradiation position, or fluorescence emitted by the fine particle of bead 206-*j* (in this case, the fine particles or beads 206-*j* are those formed of plastics containing fluorophores, so as to emit different fluorescenses, respectively) which passes the laser irradiation position, is monitored with a light detector 609 from a direction crossing the direction of laser irradiation to recognize the kind of the fine particle of bead.

An electric field is applied to an electrode for electrostatic spray 700 having slits which has been located under and near the end of the capillary, to spray the buffer solution as droplets 701 and the electrified fine particle or bead 206-*j*. A directional control plate 702 for controlling the direction of the fine particle or bead by means of the intensity of electric field is provided under the electrode for electrostatic spray 700. The controller 720 recognizes the kind of the fine particle or bead 206-*i* by information on the reflected light or fluorescence detected from the fine particle- or bead 206-*j*, selects a compartment cell 705-*j* (j=1, 2, ~, 9) for collecting the fine particle or bead 206-*j*, and determines the degree of directional control imposed on the fine particle or bead 206-*j*.

The controller 720 controls the degree and direction of movement of a moving stage for fractionating vessel 707 loaded with a fractionating vessel 706 having compartment cells 705-*j*, and collects the fine particles or beads 206-*j* into the different compartment cells 705-*j* to recover the same.

The controller 720 discriminates among the kinds of the fine particles or beads 206-*j* on the basis of information on the reflected light or fluorescence detected from each of the fine particles or beads 206-*j*, and controls the intensity of electric field applied to the directional control plate 702 and the drive of the moving stage for fractionating vessel 707.

The PCR amplification products separated and recovered are electrophoresed in the same manner as in Example 1, whereby the presence ratio among the noted target DNA fragment species in each of a plurality of DNA samples can be determined.

What is claimed is:

1. A sample preparation method for DNA analysis comprising the steps of:

amplifying, at the same time and under the same condition, a plurality of target DNA fragment species having different sequences and being originated from a plurality of DNA sample species, by polymerase chain reaction (PCR), by using a plurality of specific primers and a free primer, wherein an oligonucleotide is introduced by ligation into the 3'-end of each of said target DNA fragment species, said oligonucleotide has a common sequence at the side of the 3'-end of said oligonucleotide and a discriminating sequence which discriminates said target DNA fragment species and follows the 5'-end of said common sequence, said common sequence is common to all the target DNA fragment species and is the same irrespective the length of said target DNA fragment species and the DNA sample species, the length of said discriminating sequence depends on the DNA sample species, the length of said discriminating sequence is the same for said target DNA fragment species originated from the same DNA sample species and different for said target DNA fragment species originated from different DNA sample species, and said target DNA fragment species originated from the different DNA sample species are discriminated by the length of said discriminating sequence, each of said specific primers has a sequence complementary to any said target DNA fragment species to be amplified, said specific primers are immobilized on the surfaces of a plurality of supports separable each other so as to be separated on the base of the kinds of said specific primers, said free primer is contained in a polymcrase chain reaction solution and hybridizes with said common sequence of said oligonucleotide, and recovering the PCR amplification products on the surfaces of said supports, on the basis of the kind of target fragment species.

* * * * *